US009216245B2

(12) United States Patent
Yamashita et al.

(10) Patent No.: US 9,216,245 B2
(45) Date of Patent: Dec. 22, 2015

(54) MANUAL BREAST PUMP

(75) Inventors: Daisuke Yamashita, Tokyo (JP); Mitsuo Tashiro, Tokyo (JP)

(73) Assignee: Pigeon Corporation, Tokyo (JP)

( * ) Notice: Subject to any disclaimer, the term of this patent is extended or adjusted under 35 U.S.C. 154(b) by 0 days.

(21) Appl. No.: 14/112,182

(22) PCT Filed: Apr. 20, 2012

(86) PCT No.: PCT/JP2012/002747
§ 371 (c)(1),
(2), (4) Date: Dec. 19, 2013

(87) PCT Pub. No.: WO2012/144231
PCT Pub. Date: Oct. 26, 2012

(65) Prior Publication Data
US 2014/0100520 A1 Apr. 10, 2014

(30) Foreign Application Priority Data

Apr. 22, 2011 (JP) ................................. 2011-096080

(51) Int. Cl.
*A61M 1/06* (2006.01)
*A61M 1/00* (2006.01)

(52) U.S. Cl.
CPC ............... *A61M 1/06* (2013.01); *A61M 1/0072* (2014.02); *A61M 2205/075* (2013.01)

(58) Field of Classification Search
CPC ..... A61M 1/06; A61M 1/062; A61M 1/0072; A61M 1/066; A61M 1/065; A61M 1/0068; A61M 2205/075; A61M 2205/0071
USPC .................................................... 604/74, 76
See application file for complete search history.

(56) References Cited

U.S. PATENT DOCUMENTS 7,749,188 B2    7/2010  Tashiro et al.
2003/0204164 A1*  10/2003  Britto et al. .................... 604/74

(Continued)

FOREIGN PATENT DOCUMENTS

CN    101232909 A    7/2008
JP    4413231 B2    2/2010

(Continued)

OTHER PUBLICATIONS

International Search Report for PCT Patent App. No. PCT/JP2012/002747 (Jul. 24, 2012).

(Continued)

*Primary Examiner* — Bhisma Mehta
*Assistant Examiner* — Jenna Zhang
(74) *Attorney, Agent, or Firm* — Cermak Nakajima & McGowan LLP; Tomoko Nakajima

(57) ABSTRACT

The invention provides a manual breast pump which can be disassembled and assembled easily for cleaning purposes, and which can readily modify a negative pressure during expression of milk generated by a lever-type operating section. A breast pump having an accommodating vessel for collecting breast milk, a breast pump main body, and an operating section attached to the breast pump main body and for deforming a negative pressure generating member installed on the breast pump main body, wherein the operating section has a lever form and includes an engagement opening as an engaged section for engaging with an engaging section provided on the breast pump main body, and the engagement opening is selectively engaged with engaging sections in a plurality of positions provided midway on an extending section erected in a pillar shape as one portion of the negative pressure generating member.

3 Claims, 11 Drawing Sheets

(56) References Cited

U.S. PATENT DOCUMENTS

2007/0078383 A1* 4/2007 Tashiro et al. .................. 604/74
2008/0195039 A1* 8/2008 Kataoka et al. ................. 604/74
2010/0262072 A1* 10/2010 Attolini et al. .................. 604/74

FOREIGN PATENT DOCUMENTS

| WO | WO2007/017968 | A1 | 2/2007 |
| WO | WO2009/006627 | A2 | 1/2009 |
| WO | WO2009/063338 | A1 | 5/2009 |

OTHER PUBLICATIONS

Office Action from Chinese Patent App. No. 201280019584.6 (Mar. 31, 2015).
Supplementary European Search Report for European Patent App. No. 12774564.4 (Aug. 20, 2014).
Office Action from European Patent App. No. 12774564.4 (Jun. 17, 2015).
Most recent set of claims in European Patent App. No. 12774564.4 (Mar. 2015).

* cited by examiner

F I G. 1
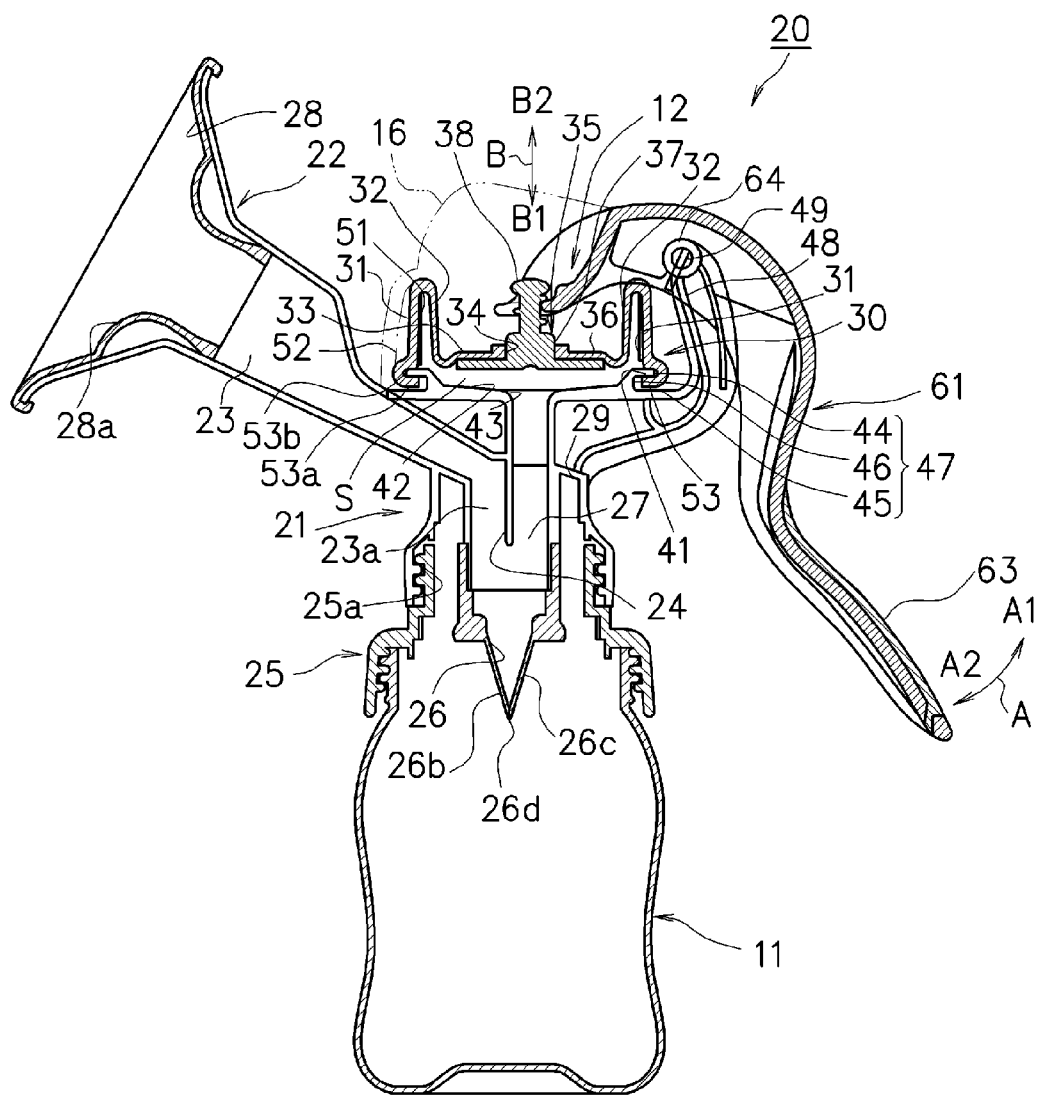

(A)

(B)

(A)

(B)

(A)

(B)

F I G. 8
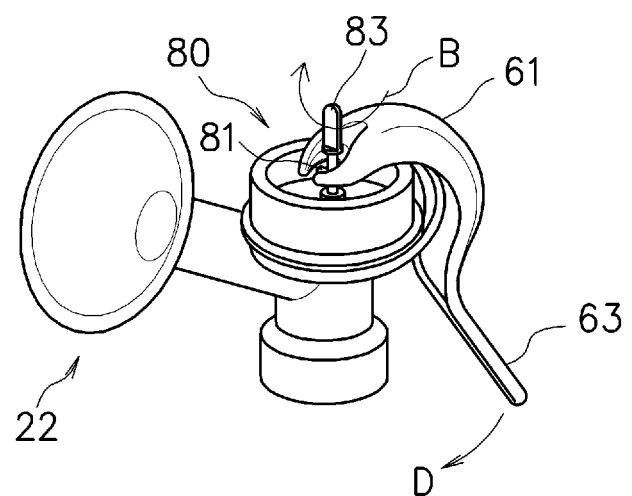

(A)

(B)

(A)

(B)

F I G. 14
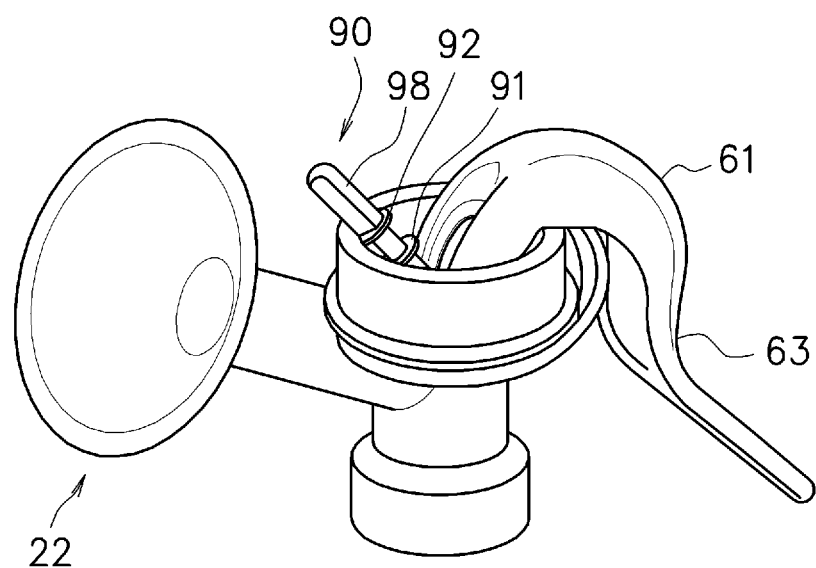

(A)

(B)

MANUAL BREAST PUMP

This application is a national phase entry under 35 U.S.C. §371 of PCT Patent Application No. PCT/JP2012/002747, filed on Apr. 20, 2012, which claims priority under 35 U.S.C. §119 to Japanese Patent Application No. 2011-096080, filed Apr. 22, 2011, both of which are incorporated by reference.

TECHNICAL FIELD

This invention relates to improvement of a manual breast pump capable of expressing milk by generating a negative pressure by a lever-shaped operating section which is operated manually, for example.

BACKGROUND ART

A breast pump provided with a milk expressing section having a diameter enlarged into a trumpet shape which is abutted against a mother's breast, in other words, an enlarged-diameter milk expressing section, is used widely.

In particular, a composition is known in which a recess is provided on an upper end, or the like, of a breast pump main body, in such a manner that breast milk which has turned into a mist due to the negative pressure during expression of milk does not leak out externally, and a deforming member, such as a diaphragm, is accommodated inside this recess.

In other words, a manual breast pump is known in which an operating section such as a handle, is coupled to a diaphragm, and a negative pressure is created by repeatedly lifting up the diaphragm by reciprocal movement of the handle; the breast pump relating to Japanese Patent No. 4413231 presented by the present applicants is one manual breast pump of this kind (Patent Document 1).

The breast pump according to Patent Document 1 can be disassembled and assembled easily for cleaning, but the operating section cannot been removed easily when operated.

Consequently, this breast pump has an accommodating vessel 11 for collecting breast milk, a breast pump main body, and a handle 61 which is attached to the breast pump main body and functions as an operating section for deforming a negative pressure generating member installed on the breast pump main body. An engaged section 62 which is positioned at one end of the handle 61 moves reciprocally up and down as indicated by the arrow B due to rotating about an axle section 49, as shown in FIG. 2 of Patent Document 1.

Here, as shown in FIG. 1, when a user operates the lever section 63 in the direction A2, in other words, so as to approach the bottle 11, and the engaged section 62 thereby moves in the direction of arrow B2, then a second wall section 32, which is a deforming section of the negative pressure generating member 30, is caused to deform so as to face towards the upper side from a state facing towards the lower side in FIG. 1. Therefore, when the volume of the internal space S formed between a bottom surface section 33 and an inclined surface 42 is increased, air from a milk expressing section air flow path 23 is drawn in, in accordance with the amount of air drawn into the internal space S, and when a user's breast is abutted against the enlarged-diameter front end of the milk expressing section 22, a hermetic space is formed, and therefore the milk expressing section air flow path 23 assumes a negative pressure. Milk is expressed by this negative pressure.

CITATION LIST

Patent Literature

Patent Document 1: Japanese Patent No. 4413231

SUMMARY OF INVENTION

Technical Problem

In the breast pump according to Patent Document 1, the magnitude of the negative pressure used for expressing milk is dependent on the stroke of the reciprocal motion of the lever section 63.

Here, as shown in FIG. 8, in the invention according to Patent Document 1, engaging sections are formed in a plurality of locations in the length direction of an extending section 75 which extends from a boss section 37 of a coupling section 35-1.

In this case, three engaging sections, namely, a first engaging section 38-1, a second engaging section 38-2, and a third engaging section 38-3 are formed, along a direction away from a position close to the boss section 37.

An engaged section 62 on the front end of the handle 61 shown in FIGS. 4A and 4B is selectively coupled to each of the engaging sections. Consequently, the engaged section 62 of the handle 61 is coupled at the respective height positions of the first positions L1, L2, L3, in accordance with the height positions of the respective engaging sections which are engaged. Therefore, the stroke of the reciprocal movement along the direction of arrow B in FIG. 2 changes, and hence the user is able to select a suitable strength in accordance with the magnitude of the negative pressure generated.

However, when the applicants made a trial manufacture of the structure of third engaging section 38-3 in actual practice, satisfactory results were not necessarily obtained.

This is because the task of selectively engaging the engaged section 62 on the front end of the handle 61 with any one of these three engaging sections, namely, the first engaging section 38-1, the second engaging section 38-2 and the third engaging section 38-3, on the inner side of the deforming section 32 which is only a narrow space, when in a concave depressed state, requires the handle to be pulled out from the bearing section of the main body, and to be engaged again in another position, and therefore further modifications are necessary in order to achieve a practicable composition.

This invention was devised in order to resolve the problems described above, an object thereof being to provide a manual breast pump which can be disassembled and assembled easily for cleaning purposes, and which can readily change the negative pressure during expression of milk which is generated by the lever-shaped operating section.

Solution to Problem

In order to achieve the aforementioned object, the present invention provides a manual breast pump having an accommodating vessel for collecting breast milk, an attachment and detachment section for attaching and detaching a breast pump main body with respect to the accommodating vessel, and a manual operating section attached to the breast pump main body and deforming a negative pressure generating member installed on the breast pump main body, wherein the breast pump main body has an enlarged-diameter milk expressing section having an enlarged diameter for abutting against a user's breast; the negative pressure generating member comprises: a coupling section which has an axle-shaped extending section extending and erected in the form of a pillar, and which couples with the operating section by an engaging section formed midway in the extending section; and a deforming section which generates the negative pressure by deforming, upon receiving a force from the coupling section; the manual operating section is a long handle and includes: a bearing section supported on an axle section provided on the breast pump main body; an engaged section which is disposed at one end of the handle and coupled with the coupling section; and a lever section which is disposed at the other end of the handle; the extending section of the coupling section comprises the engaging section which is engaged at at least a plurality of positions along the direction of extension of the extending section, and has a grippable head section at a front end side of the extending section; and the coupling section is rotatable about a virtual central axis of the extending section, and with the engaged section of the lever being engaged with the engaging section, the extending section turns about an axis, thereby a position of engaging with the engaged section of the lever section is moved in the direction of extension of the extending section.

According to the composition described above, in the breast pump according to the present invention, the enlarged-diameter milk expressing section is closed off when abutted against a user's breast, and a negative pressure for expressing milk is created inside the enlarged-diameter milk expressing section by operating the lever section of the manual operating section in this state.

Here, the axle-shaped extending section which extends from the negative pressure generating member is provided with an engaging section, and a negative pressure is created by movement of the lever which is provided with an engaged section that is engaged by the engaging section.

It has become more apparent that in order to draw out breast milk without undue force when starting to express milk, at first, a weak negative pressure can be applied to the whole breast including the vicinity of the areola, and as the user gradually becomes used to the suctioning stimulus on the breast, discharge of milk can be promoted without undue force. Furthermore, there are individual differences between the negative pressure that can be used effectively to express milk.

In view of these points, in the present invention, the extending section of the coupling section comprises the engaging section which is engaged at at least a plurality of positions along the direction of extension of the extending section, and has a grippable head section at a front end side of the extending section; and the coupling section is rotatable about a virtual central axis of the extending section, and an engaging position with the engaged section of the lever section is moved in the direction of extension of the extending section, by turning the extending section about the axis in a state where the engaged section of the lever is engaged with the engaging section. Therefore, the operating stroke of the lever can be changed by this movement, and therefore the negative pressure applied during expression of milk can be set to a weak pressure at the start of expression, and can gradually be adjusted to a stronger pressure thereafter. In accordance with this, the negative pressure during expression of milk can be adjusted easily to any pressure desired by the user.

In particular, since a grippable head section is provided at the front end of the extending section, it is possible to readily operate and rotate the extending section of the coupling section by gripping and pressing the head section.

Desirably, a composition is adopted in which the engaging section is formed in a spiral shape on an outer circumference of the extending section of the coupling section, and engages with an engaged section at one end of the handle, which is an insertion space section formed on a front end of the handle section, and a slit section provided in a depthward direction and formed in a bottom portion of this insertion space section.

According to the composition described above, by rotating the extending section axially, the spiral-shaped engaging section on the outer circumference thereof fits into the slit and moves relatively in a spiral shape, whereby the engaged position of the lever section is moved in an up/down direction, and therefore the operating stroke of the lever can be changed and the negative pressure during expression of milk can be adjusted easily to a pressure desired by the user.

Desirably, a horizontally projecting lateral axle section is formed in one portion of the circumferential direction of the extending section, as the engaging section of the coupling section, and a downward facing step section is provided at a position above the lateral axle section of the extending section, the breast pump further including, as an engaged section at one end of the handle, an insertion space section formed on a front end of the handle section, and a slit section provided in a depthward direction and formed in a bottom section of this insertion space section.

According to the composition described above, by rotating the extending section axially, the horizontally projecting lateral axle section is separated above the upper surface of the slit, or fits into the slit and separates below the slit. In a state where the horizontal lateral axle section is separated from the upper surface of the slit, if the lateral axle section is fitted into the slit and separated below the slit, then the peripheral edge of the slit abuts against the downward facing step section. The upper surface of the slit abuts against the lower portion of the lateral axle section which projects horizontally. Consequently, since the engaged position of the lever section is moved in the up/down direction, the operating stroke of the lever can be changed and the negative pressure during expression of milk can be adjusted readily to any pressure desired by the user.

Desirably, the front end section of the lateral axle section has a taper-shaped inclined guide section having a diameter that gradually decreases towards the front end.

According to the composition described above, when the engaged section of the handle is fitted onto the outer side of the extending section and rotated, the engaged section is guided by the taper-shaped inclined guide section and can be moved readily up or down the lateral axle section. In other words, since the inclined guide section of the lateral axle section has a taper shape, then the engaged section of the handle assumes a suitable shape, both when guided from top to bottom and when guided from bottom to top.

Furthermore, desirably, the present invention is a manual breast pump having an accommodating vessel for collecting breast milk, an attachment and detachment section for attaching and detaching a breast pump main body with respect to the accommodating vessel, and a manual operating section attached to the breast pump main body and deforming a negative pressure generating member installed on the breast pump main body, wherein the breast pump main body has an enlarged-diameter milk expressing section having an enlarged diameter for abutting against a user's breast; the negative pressure generating member comprises: a coupling section which has an axle-shaped extending section erected in the form of a pillar, and coupled with the operating section by an engaging section formed midway in the extending section; and a deforming section which generates the negative pressure by deforming, upon receiving a force from the coupling section; the manual operating section is a long handle and includes: a bearing section supported on an axle section provided on the breast pump main body; an engaged section which is disposed at one end of the handle and coupled with the coupling section; and a lever section disposed at the other end of the handle, and wherein, with the deforming section undergoing elastic deformation at the lower end of the coupling section, the extending section can easily be tilted down and can readily be restored to a perpendicular erect state from a tilted down state due to the elasticity of the deforming section, and at least a plurality of the engaging sections are provided on the extending section along a direction of extension of the extending section; and a grippable head section is provided at a front end of the extending section.

According to the composition described above, even in a case where the axle-shaped extending section erected in the form of a pillar on the negative pressure generating member is disposed in a narrow space, by positioning the engaged section of the operating section at the position of the coupling section and varying the up/down position of the engaged section, while using the elastic properties of the deforming section to tilt down the extending section or to restore the extending section from a tilted down state to an erect state, one of the plurality of engaging sections can be selected and engaged readily with the engaged section.

In particular, since a grippable head section is provided at the front end of the extending section, it is possible to readily operate and bend the extending section of the coupling section by gripping and pressing the head section.

BRIEF DESCRIPTION OF DRAWINGS

FIG. 1 is a schematic cross-sectional diagram of a breast pump relating to a first embodiment of the present invention.

FIG. 8 is a partial schematic perspective diagram showing an example of use of the engaging section in FIG. 6.

FIG. 14 is a partial schematic perspective diagram showing an example of use of the engaging section in FIG. 12.

DESCRIPTION OF EMBODIMENTS

Below, preferred embodiments of the invention are described in detail with reference to the accompanying drawings.

The embodiments given below are preferred concrete examples of the present invention, and therefore although various technically desirable limitations are indicated, the range of the present invention is not limited to these modes, unless it is explicitly stated in the description given below that the invention is limited.

Figure 2:
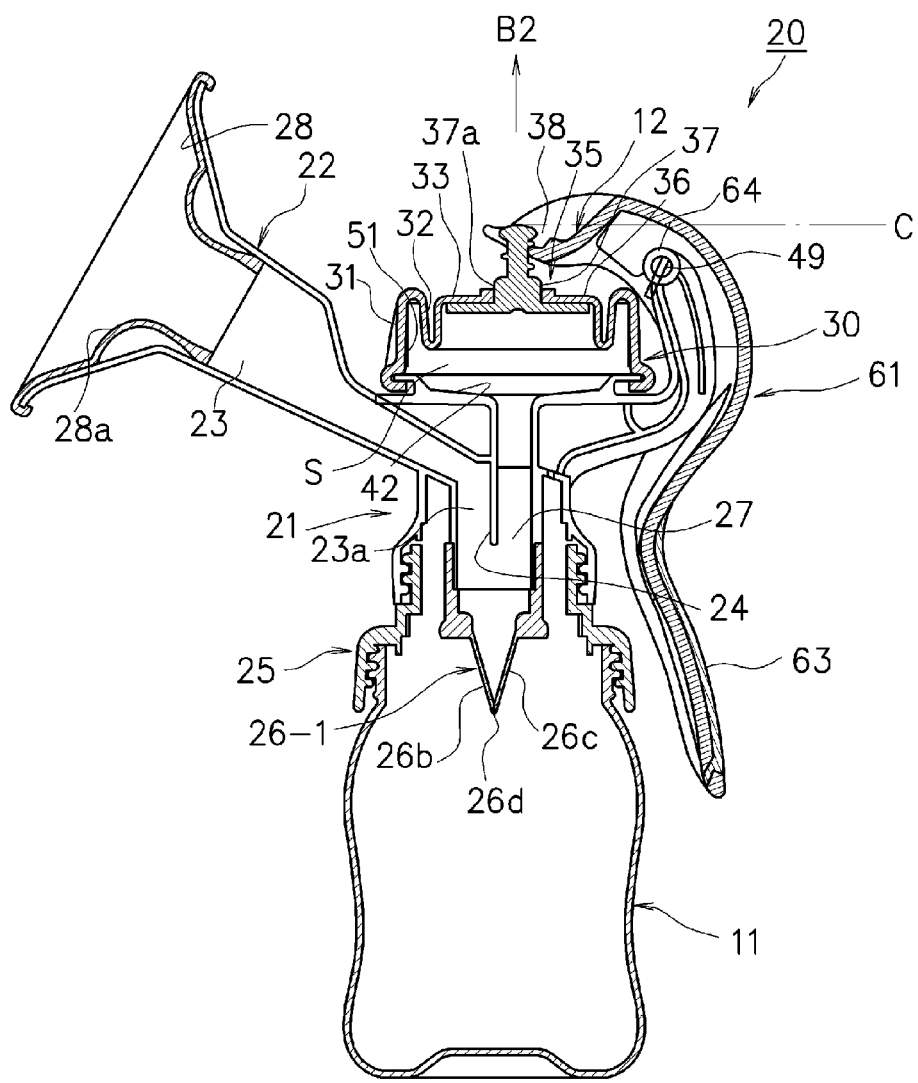
FIG. 2 is a schematic cross-sectional diagram of a breast pump relating to the first embodiment of the present invention.

FIG. 1 and FIG. 2 are general perspective drawings of a manual breast pump relating to the present invention (abbreviated to "breast pump" below), and relate to the respective embodiments of the present invention, in which the entire composition is the same.

In these drawings, the breast pump 20 is provided with a breast pump main body 21 (called "main body" below), a handle 61, which is an operating section, and a bottle 11 which is an accommodating vessel for collecting the expressed breast milk. The handle 61 can be attached to and detached from the breast pump main body 21.

Furthermore, as shown in FIG. 1, it is also possible to attach and detach a substantially dome-shaped hood 16 on an upper section where a negative pressure generating member 30 of the main body 21 is mounted.

The hood 16 is cut out in the location of the handle 61 and can cover and protect the negative pressure generating member 30, or the like, by being fitted so as to avoid the handle 61. It is also possible to adopt a composition which does not include the hood 16.

The whole of the main body 21 is made from synthetic resin material which is relatively light and robust; for example, the main body 21 is made from polypropylene, polycarbonate, polycyclo-olefin, polyether sulfone, polyphenyl sulfone, or the like.

The main body 21 is provided with an attachment and detachment section 25 for attaching to and detaching from the bottle 11. The attachment and detachment section 25 is, for example, a flat tubular portion as shown in FIG. 2, which has a female thread section 25a on the inner side, so as to threadedly engage with a male thread section formed on the circumference of a mouth of the bottle 11.

The bottle 11 may be a product specially made for the breast pump 20 or may use a feeding bottle which is compatible with the attachment and detachment section 25, or may be a bag-shaped member, rather than a formed vessel.

A conical or trumpet-shaped enlarged-diameter milk expressing section 22 having a front end which opens to a large diameter is provided in an obliquely inclined state on top of the attachment and detachment section 25 of the main body 21. A shock absorbing section 28, which is an elastic body made of silicone rubber, elastomer, natural rubber, or the like, is attached detachably to the opening side of the enlarged-diameter milk expressing section 22. The shock absorbing section 28 reduces the stimulus produced when the enlarged-diameter milk expressing section 22 abuts against the breast during expression of milk, so as not to cause pain. A projecting section 28*a* which applies a stimulus to the vicinity of the areola of the user is formed at a plurality of locations on the inner circumferential surface of the shock absorbing section 28, for example, in two positions on the upper and lower sides.

The milk expressing section air flow path 23 of the enlarged-diameter milk expressing section 22 is a flow path for air and expressed breast milk, which bends downwards towards the bottle 11. Furthermore, the opening of the milk expressing section air flow path 23 of the enlarged-diameter milk expressing section 22 is located on the inner side of the attachment and detachment section 25 between the main body 21 and the bottle 11, and a small chamber 26 is attached thereto. Moreover, a further air flow path 27 is provided via a partition wall 24, adjacently to a downward facing portion 23*a* of the milk expressing section air flow path 23. As shown in the figures, the lower end opening of the air flow path 27 communicates with the downward facing portion 23*a* of the milk expressing section air flow path inside the small chamber 26.

The upper end of the air flow path 27 has an opening 43, as shown in FIG. 1, and is formed into a mounting section 41 which enlarges in a substantially circular shape so as to surround the opening 43. The mounting section 41 is a portion where the negative pressure generating member 30 is installed. The negative pressure generating member 30 is described in detail below.

The upper surface of this mounting section 41 is formed as an inclined surface 42 which is inclined so as to descend slightly towards the opening 43.

As shown in FIG. 1 and FIG. 2, the small chamber 26 is a hollow cup-shaped member which is made entirely from an elastic body of silicone rubber, an elastomer, natural rubber, or the like, and both side walls 26*b*, 26*c* on the lower end side thereof are valve elements which constitute inclined walls of the elastic body that are formed to a small thickness and gradually approach each other towards the lower end. A slit 26*d* is provided on the lower end where the two side walls 26*b*, 26*c* approach each other, and when a prescribed amount of expressed breast milk has been collected inside the small chamber 26, then due to the weight of the collected milk and the change in pressure when the negative pressure is released, as described below, the slit 26*d* opens, and the breast milk drops down inside the bottle 11. Furthermore, since a slit 26*d* is formed at the lower end of the inclined walls, then when negative pressure is applied, the air inside the bottle 11 is prevented from entering into the small chamber 26.

Moreover, a small ventilation hole 29 which communicates the interior of the bottle 11 with the outside air is formed at a location adjacent to the attachment and detachment section 25 of the breast pump main body 21, so that pressure occurring when the breast milk has collected inside the bottle 11 can escape.

The negative pressure generating member 30 has an overall form close to that of a relatively flat round cylindrical body having a bottom.

Figure 5:
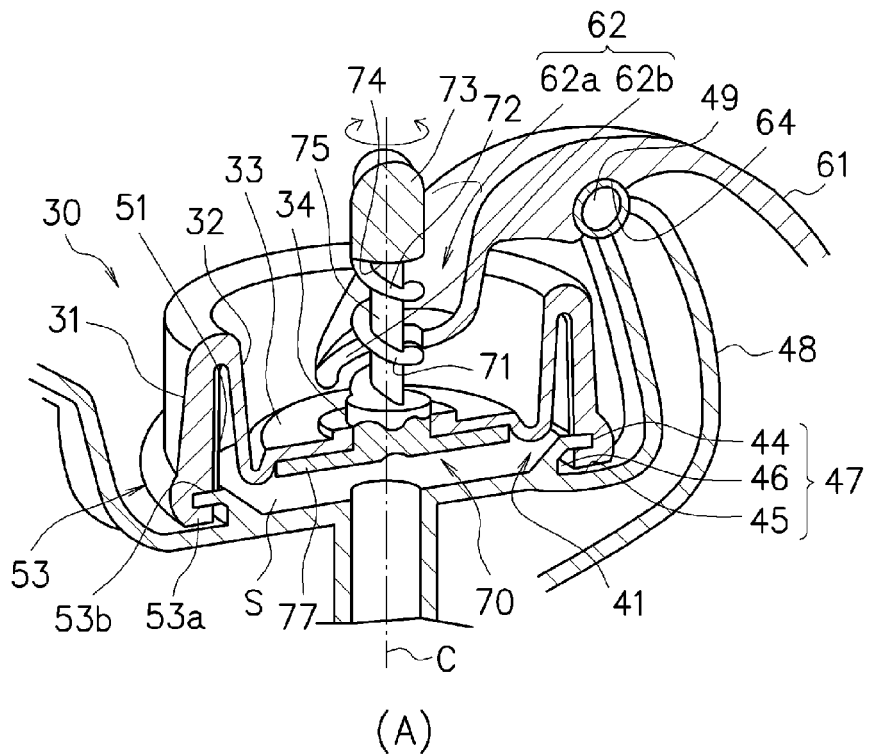
FIGS. 5A and 5B are partial enlarged cross-sectional diagrams showing a state where the engaging section in FIG. 3 and the engaged section on the operating section are intermeshed and engaged.
Figure 5:
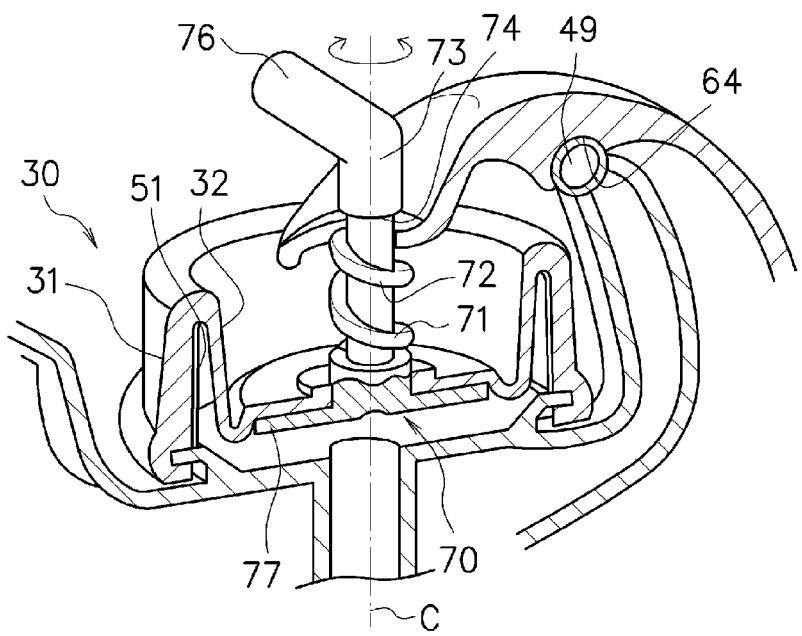

More specifically, as shown in FIGS. 5A and 5B, the negative pressure generating member 30 has a first wall section 31 which is erected on an outer side and provides sufficient rigidity to maintain the outer diameter, and a second wall section 32 which is an inside wall section of which the upper end portion is bent back to the inner side in an integrated fashion, and the portion forward of the bent back portion is formed with a small thickness. The second wall section 32 is a deforming section, the lower end of which forms a bottom surface section 33, which is a relatively broad inner bottom section provided to extend in an integrated fashion so as to close off the lower portion of the round cylindrical shape.

More specifically, the first wall section 31 and the second wall section 32 are made from the same material, but different rigidities are imparted by varying the thickness of the material. In other words, the first wall section 31 is made thicker than the second wall section 32. Therefore, when an external force is applied, the second wall section 32 is able to deform at an external force of a level that does not cause deformation of the first wall section 31. However, the second wall section 32 which is connected in an integrated fashion to the first wall section 31 covering the outer circumference thereof is arranged to the inner side in the form of a cylinder having a bottom, and ensures that a certain negative pressure is generated upon receiving an action of the operating section, as described below.

Instead of or in addition to the composition described above, it is also possible to vary the material used for the first wall section 31 and the second wall section 32, and to form the whole member by two-part molding, using a material having a lower rigidity than the first wall section for the second wall section 32.

The description will now be given with reference to FIG. 1 and FIGS. 5A and 5B.

As described below, when the handle 61 is operated, in the negative pressure generating member 30, the second wall section 32, which is the deforming section, deforms and the volume of the internal space S which is formed between the bottom surface section 33 and the mounting section 41 changes, thereby making it possible to create a negative pressure by suctioning air inside the milk expressing section air flow path 23 which is communicated with the internal space S via the air flow path 27 and the small chamber 26 (see the state in FIG. 2).

In this case, the wall section, in other words, the first wall section 31 hardly deforms at all, and hence the state of installation with respect to the mounting section 41 can be maintained.

A projecting section 51 is provided on the opposing surfaces of the first wall section 31 and the second wall section 32, which is the deforming section, and extends in a longitudinal direction so as to be interposed between these wall sections. Here, the projecting section 51 is formed on the inner surface side of the first wall section 31. When the second wall section 32, which is the deforming section, repeatedly deforms and then is restored to its original shape, during this restoring motion, an operating sound is produced when the opposing surfaces of the second wall section 32 and the first wall section 31 abut against each other, but the presence of the projecting section 51 effectively prevents this sound from becoming an unpleasant sound.

In order to deform the second wall section 32, which is a deforming section, a coupling section (member) 70 is provided. The coupling section (member) 70 is made from a hard material which is different to the second wall section 32, which is a deforming section.

The coupling section (member) 70 is called "coupling section 70" when considered as a portion of the breast pump 20, and is called "coupling member 70" when considered as a constituent member or component of the coupling section 70.

The coupling section (member) 70 is made entirely from a relatively hard synthetic resin, such as polypropylene, polycarbonate, polycyclo-olefin, polyether sulfone, or the like, and has a low flat circular disk-shaped base section 77 of which the base end section is enlarged to a broad diameter. Furthermore, the coupling section (member) 70 has an extending section 75 which is formed in an integrated fashion on top of the base section 77 and which extends in the form of an axle via a boss-shaped section which projects to a relatively low height.

Figure 3:
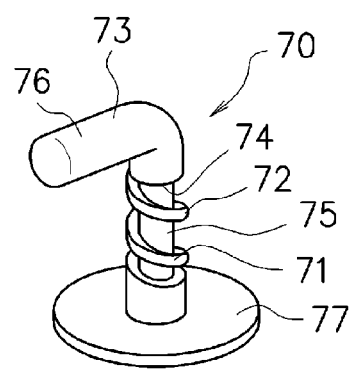
FIG. 3 is an enlarged perspective diagram showing a structure of an engaging section according to the embodiment in FIG. 1.

FIG. 3 is an enlarged perspective diagram of a coupling member 70 relating to a first embodiment of the invention.

As shown in FIG. 3, the coupling member 70 is installed rotatably as indicated by the arrow about a virtual central axis C of the extending section 75, as shown in FIGS. 5A and 5B. The coupling member 70 is composed to engage with a slit section provided in a depthward direction, which is formed in a bottom section of an insertion space portion formed on the front end of the lever section of the handle 61 (see FIG. 11), described below, that acts as an operating section. By turning the extending section 75 axially while in this engaged state, it is possible to move the engaging position with the engaged section on one end of the handle, in the direction of extension of the extending section, in other words, in the up/down direction in FIG. 1 or FIG. 2. This point is described in detail below.

A through hole or a clearance hole 34 is formed in a central portion of the bottom surface section 33.

In other words, since the negative pressure generating member 30 and the coupling member 70 are formed as separate bodies, then reference numeral 34 is a clearance hole, and by setting the clearance hole 34 to have a slightly smaller internal diameter than the external diameter of the extending section 75 and the boss section 37 of the coupling member 70, in such a manner that the extending section 75 and the boss section 37 can be inserted therethrough, and by inserting the boss section 37 from the rear surface of the bottom surface section 33, attachment can be performed very easily, while reliably ensuring airtight properties. In this case, detachment for the purpose of cleaning, or the like, can also be performed easily.

Moreover, by making the coupling section 70 separate from the bottom surface section 33, it is easy to achieve a structure in which the coupling section 70 rotates axially with respect to the bottom surface section 33.

On the other hand, the coupling section of the third embodiment, which is described hereinafter, can be formed in an integrated fashion with respect to the bottom surface section 33.

Furthermore, as shown in FIGS. 5A and 5B, the negative pressure generating member 30 is attached to and detached from a peripheral edge section 47 of the mounting section 41, by an attachment and detachment section 53 which is formed in a substantially circular shape, the peripheral edge section 47 being formed with a diameter slightly larger than the attachment and detachment section 53.

The attachment and detachment section 53 of the negative pressure generating member 30 has an inward facing flange 53*a*, which is a negative pressure generating side flange section that projects inwards at the lower end thereof, by the first wall section 31 extending downwards and being bent inwards, and an inner groove 53*b* which is a negative pressure generating side groove section which is formed on the upper side and the inner side of the flange 53*a*. The whole of the attachment and detachment section 53 has a prescribed rubber-like elasticity.

On the other hand, an outward facing dual flange is formed on the peripheral edge section 47 of the mounting section 41. More specifically, the mounting section 41 is provided with a first flange 44, which is an outwardly projecting main body side flange section on the upper end of the mounting section 41 and a second flange 45 which is a positioning device positioned below the first flange 44 and having an outer diameter larger than the lower end of the attachment and detachment section 53 and the first flange 44, and furthermore an outer groove 46 which is open on the outer side is formed, this outer groove 46 being a main body side groove section that is indented to the inner side by reducing the diameter in the gap between the first flange 44 and the second flange 45.

A user grips the side surfaces constituted by the first wall section 31 and the second wall section 32 of the negative pressure generating member 30, and causes the outer surface of the inward facing flange 53*a*, which is the lower end of the attachment and detachment section 53 positioned on the opposite side to the gripped position, to abut against an upward facing step section of the second flange 45, which is a positioning device. In a state where the inward facing flange 53*a* is engaged inside the outer groove 46, the user pulls and tenses the negative pressure generating member 30 with her gripping hand while lightly pressing down on the engaged position with a finger of the non-gripping hand. Consequently, the inward facing flange 53*a* in the portion other than the engaged position deforms and rides up over the first flange 44 and enters into the main body side groove section 46. In so doing, the whole of the attachment and detachment section 53 becomes installed on the peripheral edge section 47, the first flange 44 enters into the inner groove 53*b*, and furthermore, the inward facing flange 53*a* also enters into the outer groove 46, whereby an installation that remains hermetically sealed is achieved.

Consequently, the negative pressure generating member 30 is installed very easily. In other words, the second flange 45 is formed at a position which is distanced slightly further from the first flange 44 than the thickness of the inward facing flange 53*a*, and when the negative pressure generating member 30 is installed, the second flange 45 serves as a projecting rib that prevents the inward facing flange 53*a* from riding up over the outer groove 46.

Furthermore, when, conversely, the negative pressure generating member 30 is removed, by simply holding the first wall section 31 by hand and stretching outwards, the inward facing flange 53*a* is removed from the outer groove 46 and rides up over the first flange 44, and therefore removal can be performed very easily.

In the present embodiment, the second flange 45 has a similar shape to the first flange 44, but it may also be formed with a portion that project beyond the first flange 44, in a part thereof; for example, it is also possible to adopt a composition in which a cutaway is formed in a side edge so as to facilitate the action of pressing with the other finger.

Here, the first wall section 31, the second wall section 32 and the bottom surface section 33 of the negative pressure generating member 30 are desirably made entirely as a single body from a soft material having very good relative elasticity, in other words, a synthetic resin having a hardness of approximately HS30 to 70 as measured by an A-type durometer according to JIS-K6253 (ISO 7619), or an elastomer such as silicone rubber, isoprene rubber, or SEBS (styrene-ethylene-butylene-styrene), for example.

Moreover, desirably, the thickness of the material constituting the portion of the first wall section 31 is 1.5 mm to 3.0 mm, and the thickness of the material constituting the second wall section 32 is 1.0 mm to 2.5 mm.

If the hardness of the negative pressure generating member 30 is smaller than 30, then the deformation of the first wall section 31 and the generated negative pressure both become small. If the hardness exceeds 60, then the force required to operate the handle 61 as described below becomes large, and the operation for creating a negative pressure becomes very difficult.

If the thickness of the second wall section 32 is smaller than 1.0 mm, then the extension due to rubber elasticity upon deformation becomes larger, and the generated negative pressure becomes smaller. If the thickness exceeds 2.5 mm, then the force required to operate the handle 61 as described below becomes large, and the operation for creating a negative pressure becomes very difficult.

If the thickness of the first wall section 31 is smaller than 1.5 mm, then the wall section will buckle during the creation of a negative pressure. In other words, unwanted deformation occurs and a sufficient negative pressure cannot be generated. If the thickness of the first wall section 31 exceeds 3.0 mm, then the wall section cannot deform sufficiently during installation on the breast pump main body 21, and hence installation becomes difficult to perform.

As shown in FIG. 1, FIG. 2 and FIGS. 5A and 5B, in the upper portion of the main body 21, an arm 48 for attaching the handle 61, and an axle section 49 formed on the front end thereof, extend at a position opposite to the position where the milk expressing section 22 extends. The arm 48 is located at a position whereby the front end thereof is adjacent to the negative pressure generating member 30 and is located above the upper end of the negative pressure generating member 30. In this embodiment, an axle section 49 is provided on the front end of the arm 48.

Figure 11:
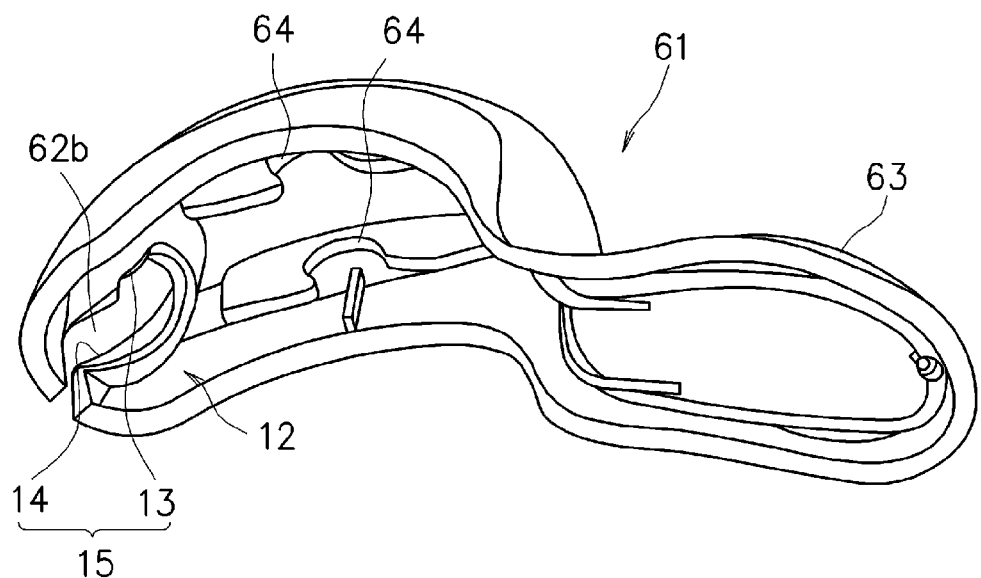
FIG. 11 is a schematic perspective diagram of a manual operating section which is used in an embodiment of the present invention.

A bearing section 64 which is described in FIG. 11 is supported rotatably, in an attachable and detachable state, on the axle section 49.

FIG. 11 is a schematic perspective diagram looking up through the handle 61 in a state where the inner side of the handle 61 is facing downwards and is arranged in a virtual horizontal plane.

The handle 61 has a long shape as shown in FIG. 11, for example, and is formed entirely as a molded part made as a single body from a light and relatively robust synthetic resin, for example, polypropylene, polycarbonate, polycyclo-olefin, polyether sulfone, and the like. An engaged section, which is described hereinafter, is provided on an upper end, which is one end of the handle 61. As shown in FIG. 11, the engaged section 12 is provided in the vicinity of the front end of the handle 61. The engaged section 12 includes an engagement opening 15 formed on the front end side, which is one end of the handle section 61. This engagement opening 15 includes an insertion opening section 13, which is an opening larger than the outer shape of the engaging section 38, formed on the side of the bearing section 64 in a state where at least the handle 61 is installed on the breast pump 20 as shown in FIG. 1, and a holding opening section 14, which is an opening smaller than the outer shape of the engaging section 38, provided adjacently to the insertion opening section 13 and to the front end side from same. A slit 62b is formed in the holding opening section 14.

The lower end 63, which is the other end of the handle 61, has a lever shape, and serves as a handle, and when a user holds and grips this lower end 63 at a position on her palm between the thumb and index finger, and presses in the direction A2 in FIG. 1, the deforming section 30, described below, is pulled up, thereby creating a negative pressure for expressing milk, and when the user lessens the gripping force, the deforming section 30 returns in the direction of arrow A1, and the deforming section 30, which has deformed elastically, is restored to its original shape.

A characterizing feature of this embodiment is that the size of the restoring movement in the direction of A1 from the movement in the direction A2, in other words, the operating stroke of the lever section 63, can be changed easily.

In other words, as shown in FIGS. 5A and 5B and FIG. 11, an insertion space section 62a which is formed on the front end of the handle 61 as an engaged section 62 is provided on one end side of the handle 61, and a slit section 62b which is provided in a depthward direction is formed in a bottom portion of this insertion space section 62a.

The insertion space section 62a is a concave space which is open on the upper side. The slit section 62b is a slit cut so as to face the depthward direction from the one end section, and on both edge portions of this slit, an upward facing step section of narrow width capable of engaging with the engaging section is formed extending in the depthward direction.

As described below, the handle 61 can be attached and detached easily by means of the engaged section 62 with respect to the engaging section of the coupling section (member) 70. The other end 63 of the handle 61 is positioned on the lower side and projects slightly to the outside, as illustrated in FIG. 1, and has a lever-shaped external form overall.

The handle 61 is attached and detached with respect to the main body 21, and in the fixed state in FIG. 1, the handle 61 is installed rotatably, and can be attached and detached with respect to the axle section 49 at the front end of the arm 48 by a pair of bearing sections 64 which are provided at a position towards one end of the handle 61.

A non-slip portion is formed on the outer side surface of the other end of the handle 61 by using an elastic material, or the like, and two-part molding, or the like, and by means of the operator holding and operating this position, the handle 61 performs a reciprocal movement of approaching and moving away from the bottle 11, as indicated by the arrow A in FIG. 2. The non-slip portion does not have to be made from a different material, and it is possible to apply processing for raising the frictional force so to avoid slipping by providing undulations, such as bosses or ribs on the surface of the handle 61 at the corresponding location.

In accordance with this, the engaged section 62 at the front end of the handle 61 performs an upward and downward reciprocal motion as indicated by arrow B, by rotating about the axle section 49. When the user operates the handle 61 so as to approach the bottle 11 and the handle 61 moves in the direction of arrow B2, the second wall section 32 which is the deforming section of the negative pressure generating member 30 is deformed so as to face upwards from the downward facing state shown in FIG. 2. Therefore, when the volume of the internal space S formed between the bottom surface section 33 and the mounting section 41 is increased, air in the milk expressing section air flow path 23 is drawn in, in accordance with the amount of air drawn into the internal space S, and when a user's breast is abutted against the enlarged-diameter front end of the milk expressing section 22, a hermetic space is formed, and therefore the milk expressing section air flow path 23 assumes a negative pressure.

Due to this negative pressure, the expressed breast milk enters into the small chamber 26 from the downward facing portion 23a of the milk expressing section air flow path, and a certain amount of breast milk collects in the small chamber 26. In this case, since the side walls 26b and 26c are formed thin, then the side walls 26b and 26c deform to some extent in a mutually approaching direction due to the negative pressure, so the slit 26d reliably assumes a hermetically sealed state and therefore the breast milk does not leak out.

When the user operates the handle 61 to a state of closest approach to the bottle 11, the upper end 62 moves to a limit position C shown in FIG. 2, the inside end portion of the handle 61 abuts against the outer edge of a positioning section 45 opposing same, and the handle cannot be moved further and stops in an intermediately pulled-up state.

If the user loosens the force applied to the handle 61 from this state, then due to the force seeking to revert the second wall section 32, the upper end 62 moves in the direction of arrow B1, the handle 61 moves in a direction away from the bottle 11, and the second wall section 32, which is the deforming section of the negative pressure generating member 30, is restored to the state shown in FIG. 1. Therefore, the volume of the internal space S formed between the bottom surface section 33 and the mounting section 41 decreases, and due to the change in pressure caused by the release of the negative pressure, as well as the weight of the collected breast milk, the front end sides of the side walls 26*b* and 26*c* open, the slit 26*d* opens and breast milk drops down into the bottle 11.

By repeating the operation described above, with the operation of the handle 61, a negative pressure is applied in a pulsating fashion on the basis of the action of the negative pressure generating member 30, and milk is expressed.

The coupling member 70 provided on the negative pressure generating member 30 which is the central part of this action will now be described in detail with reference to FIG. 3.

FIG. 3 shows the state of the coupling member 70 relating to the first embodiment, and as shown in FIGS. 5A and 5B, the whole of this coupling member 70 is attached rotatably as indicated by the arrow about a virtual central axis C of the extending section, with respect to the deforming section 32.

The axle-shaped extending section 75 which is erected perpendicularly from the coupling member 70 has the shape of a thin pillar, and forms a screw-shaped pillar. More specifically, engaging sections 71, 72, known as "ribs", which extend in a spiral shape rotating in an axial direction are provided on the outer circumference of the extending section 75, so as to form a continuous raised portion like ridges.

A head section 73 having an enlarged diameter that can be gripped by a person's hand is formed on the front end portion of the extending section 75, and a knob 76, which is a hook-shaped portion formed by bending the end portion in a horizontal direction, is formed on the head 73. Instead of the hook-shaped knob 76, it is also possible to employ various other modes which afford easy gripping, such as a large head section which can be gripped readily, or a head section which is enlarged into a butterfly shape.

A downward facing step section 74 is formed on the lower end portion of the head section 73.

Two engaging sections constituted by spiral-shaped ribs are formed here, as indicated by reference numerals 71 and 72, but the invention is not limited to this and it is of course also possible to form three or more engaging sections.

The first embodiment is composed as described above, and the characteristic action thereof is described next.

Figure 4:
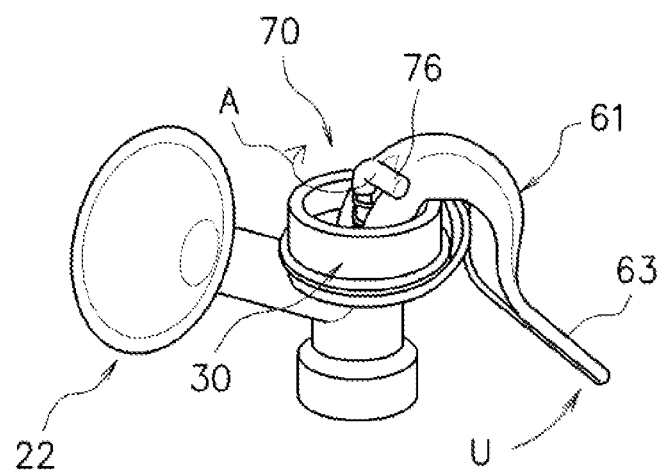
FIGS. 4A and 4B are partial schematic perspective diagrams showing an example of use of the engaging section in FIG. 3.
Figure 4:
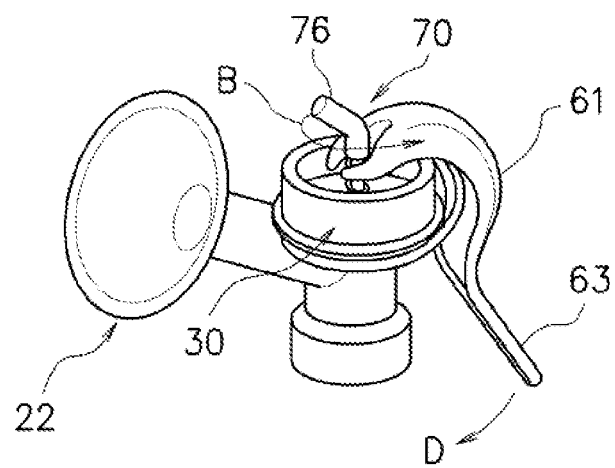

FIGS. 4A and 4B show states where the handle 61 has been engaged with the coupling member 70; in FIG. 4A, the upper end of the handle section 61 is inserted deeply into the narrow bottomed cylinder of the deforming section 30, and the slit in the engaged section thereof is engaged with the engaging section 71, which is the rib shown in FIG. 3.

In this state, the lower end 63 on the other end of the handle 61 is located at a relatively upper position as indicated by the arrow U, and therefore when moved in the direction of the arrow A2 in FIG. 1, a relatively large stroke is possible and the negative pressure created during expression of milk is accordingly larger.

On the other hand, in FIG. 4A, if the user grips the knob 76 and turns in the direction of arrow A (in the clockwise direction), then the slit 62*b* in the engaged section of the handle section 61 rises up along the direction of extension of the extending section 75 in FIG. 3, is guided by the spiral-shaped rib, and engages with the rib 72 or the downward facing step section 74. Therefore, as shown in FIG. 4B, the lower end 63 on the other end of the handle 61 is located at a relatively low position as indicated by the arrow D, and therefore when moved in the direction of the arrow A2 in FIG. 1, a relatively small stroke is possible and the negative pressure created during expression of milk is accordingly smaller.

On the contrary, in FIG. 4B, if the user grips the knob 76 and turns in the direction of arrow B (in the counter-clockwise direction), then the slit 62*b* in the engaged section of the handle section 61 descends along the direction of extension of the extending section 75 in FIG. 3, is guided by the spiral-shaped rib, and engages with the rib 71. Therefore, the handle 61 returns to the state in FIG. 4A, in which the lower end 63 on the other end of the handle 61 is located at a relatively upper position as indicated by the arrow U, and therefore when moved in the direction of the arrow A2 in FIG. 1, a relatively large stroke is possible and the negative pressure created during expression of milk is accordingly larger.

An enlarged cross-sectional diagram of the state in FIG. 4A is depicted in FIG. 5A, and an enlarged cross-sectional diagram of the state in FIG. 4B is depicted in FIG. 5B.

In this way, the user is able to move the engaging position upwards and downwards easily on the inside of the narrow deforming section 30, without having to the change the coupling position of the engaged section of the handle 61 by detaching the handle. Consequently, the operating stroke of the handle 61 can be changed easily, and therefore a negative pressure suited to the user's preferences can be set simply and easily, just by rotating and adjusting the coupling member 70.

In other words, it has become more apparent that in order to draw out breast milk without undue force when starting to express milk, at first, a weak negative pressure can be applied to the whole breast including the vicinity of the areola, and as the user gradually becomes used to the suctioning stimulus on the breast, discharge of milk can be promoted without undue force.

In this embodiment, as described above, the operating stroke of the lever can be changed as desired, and therefore the negative pressure applied during expression of milk can be set to a weak pressure at the start of expression, and can gradually be adjusted to a stronger pressure thereafter. In accordance with this, the negative pressure during expression of milk can be adjusted easily to any pressure desired by the user.

In particular, since the knob 76, which is a hook-shaped portion, is formed on the front end of the extending section 75, then this portion can be gripped easily by the user with her hand, and twisted so as to rotate about a virtual central axis of the extending section, and therefore is very easy to operate.

Figure 6:
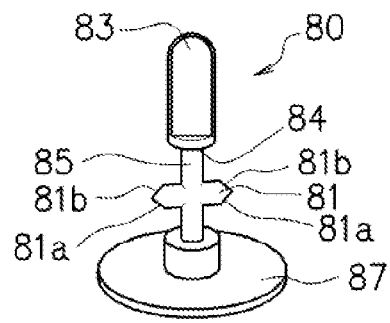
FIG. 6 is an enlarged perspective diagram showing the structure of an engaging section relating to a second embodiment of the present invention.

FIG. 6 is an enlarged perspective diagram showing the structure of a coupling member relating to a second embodiment of the invention.

Figure 9:
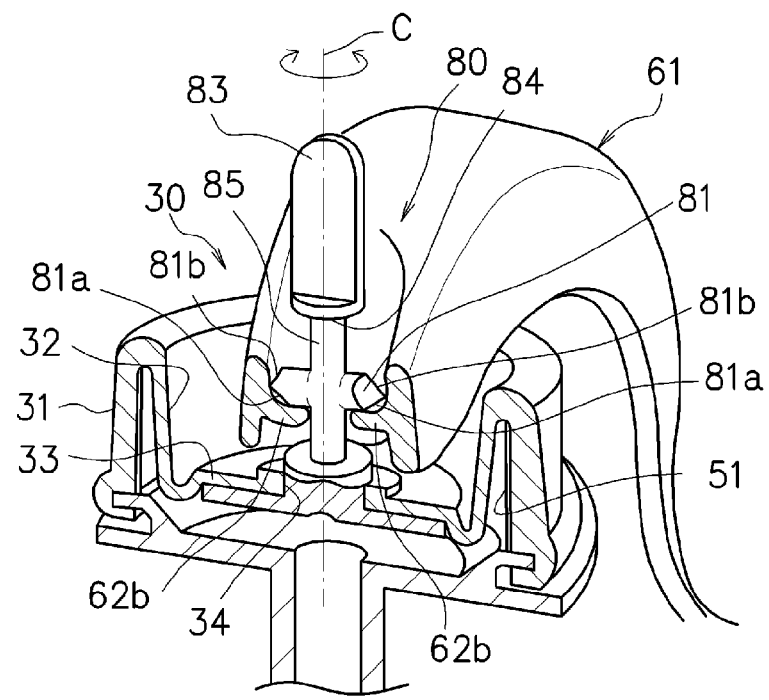
FIGS. 9A and 9B are partial enlarged cross-sectional diagrams showing a state where the engaging section in FIG. 6 and the engaged section on the operating section are intermeshed and engaged.
Figure 9:
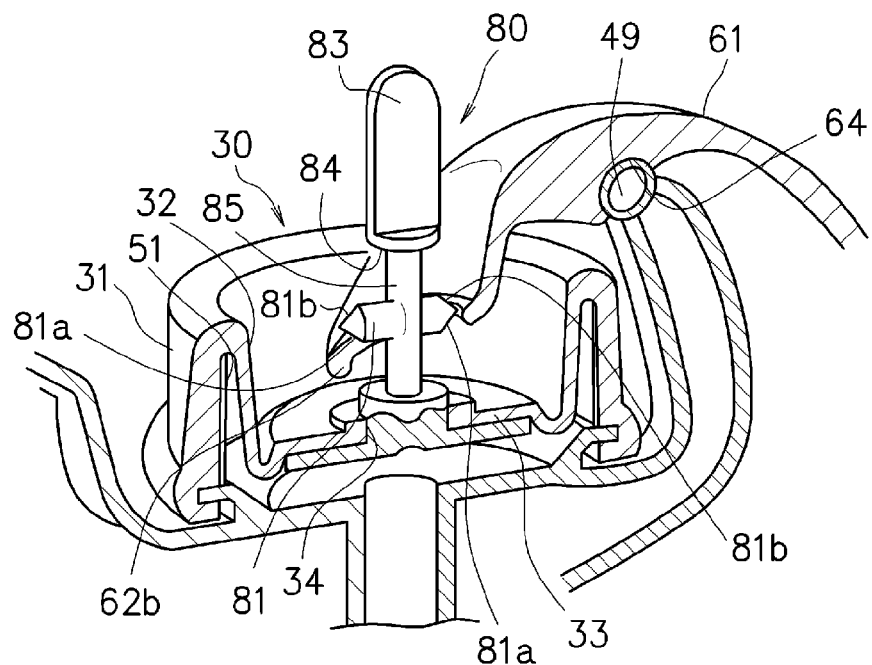
Figure 10:
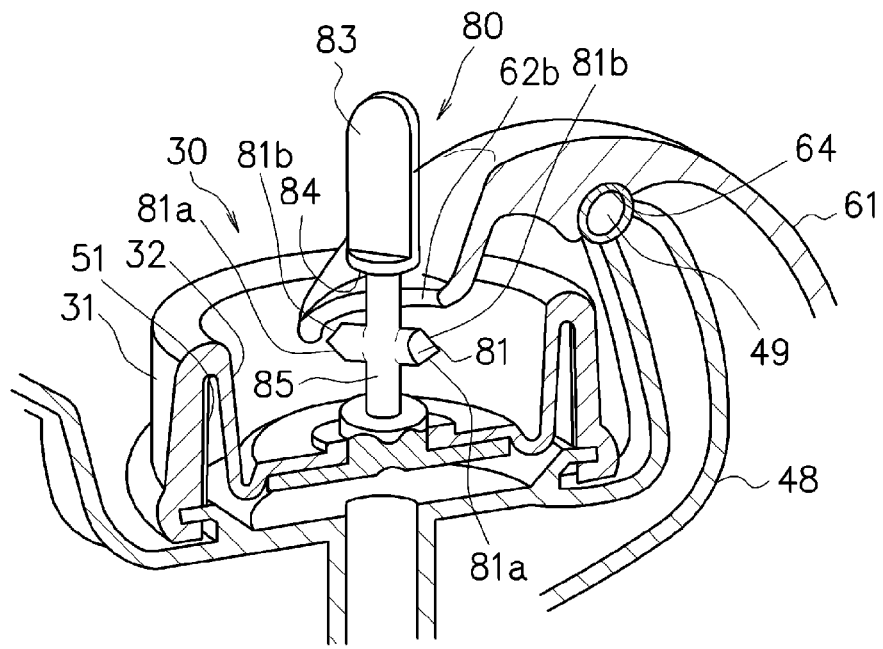
FIG. 10 is a partial enlarged cross-sectional diagram showing a state where the engaging section in FIG. 6 and the engaged section on the operating section are intermeshed and engaged.

As shown in FIGS. 9A and 9B, this coupling member 80 is also installed in such a manner that the whole thereof can rotate as indicated by the arrow about the virtual central axis C of the axle-shaped extending section, with respect to the deforming section 32.

In this coupling member 80, a horizontally projecting lateral axle section 81 is formed in one portion of the circumferential direction of the extending section 85, a head section 83 of enlarged diameter is provided at a position above the lateral axle section 81 in the extending section 85, and in the present embodiment, on the upper end portion thereof, and the lower surface of the head section 83 forms a downward facing step section 84.

In the present embodiment, the lateral axle section 81 extends horizontally in a perpendicular direction to the extending section 85 and has the structure of a cross-shaped horizontal frame.

The head section 83 provided on the front end section of the extending section 85 is a circular shape which is sufficiently large to be gripped by the user's hand and which extends to a long dimension in the vertical direction, and taking account in particular of the ease of gripping, the head section 83 is formed as a thin plate having a reduced thickness.

Furthermore, the front end section of either side of the lateral axle section 81 described above is formed as an inclined guide section having a tapered shape or a conical shape which reduces in diameter towards the front end. This inclined guide section includes upper side inclined guide sections 81b, 81b which descend gradually towards the front end, and lower side inclined guide sections 81a which ascend gradually towards the front end.

The description will now be given with reference to FIGS. 7A and 7B and FIG. 8.

Figure 7:
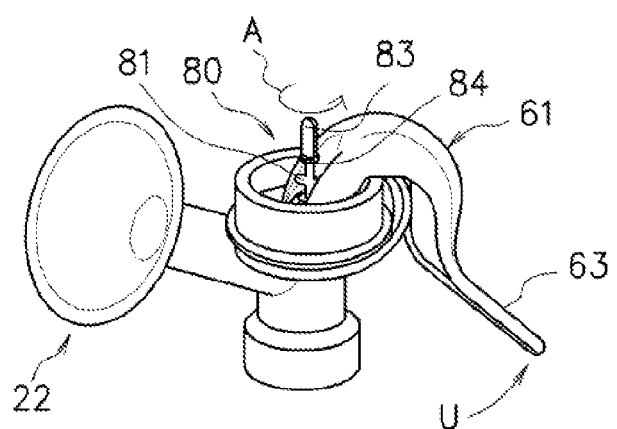
FIGS. 7A and 7B are partial schematic perspective diagrams showing an example of use of the engaging section in FIG. 6.
Figure 7:
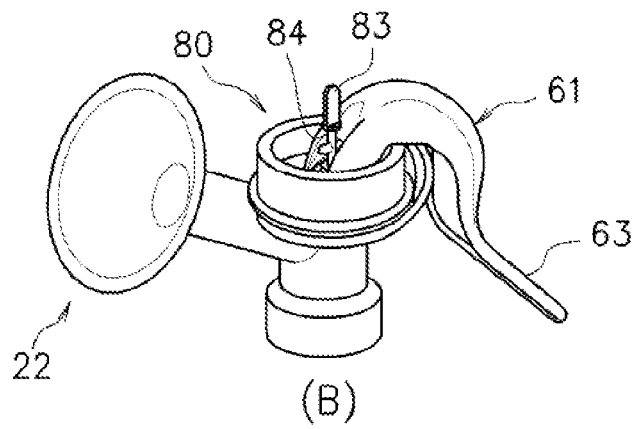

FIGS. 7A and 7B show states where the handle 61 has been engaged with the coupling member 80; in FIG. 7A, the upper end of the handle section 61 is inserted deeply into the narrow bottomed cylinder of the deforming section 30, and the slit in the engaged section thereof is engaged with the engaging section 81, which is the lateral axle section shown in FIG. 6. FIGS. 9A and 9B show enlarged partial cross-sectional diagrams of this state.

In FIG. 7A, the lateral axle 81, which is the engaging section of the coupling section 80, is engaged by being placed on top of the slit 62b, which is the engaged section of the handle section 61. FIG. 9A shows a partial enlarged cross-sectional diagram of this state.

When the head section 83 is gripped and twisted in the direction of arrow A in FIGS. 7A and 7B (the clockwise direction), the state in FIG. 7B is achieved, and the lateral axle 81 assumes a state in which the lengthwise direction thereof is aligned with the direction of extension of the slit in the handle 61, whereby the engagement can be released. FIG. 9B shows an enlarged cross-sectional diagram of this state.

When the engaged section of the handle 61 is moved so as to slide slightly upwards as shown in FIG. 8 while remaining abutted against the extending section 85, the coupling section 80 is restored from a twisted state due to the elasticity of the deforming section to which the coupling section 80 is fixed, and the lateral axle 81 can be engaged due to the slit 62b of the engaged section abutting against the downward facing step section 84 of the head section 83. In this way, the engaging position of the engaged section of the handle 61 can be changed.

More specifically, by gripping and twisting the head section 83 as shown in FIG. 9A, the lower side inclined guide sections 81a of the lateral axle section 81 of the extending section ride up over the slit 62b in the handle 61, and ride up over the upper step section of the slit 62b, thereby engaging the handle 61 at a location where a large stroke is obtained.

Moreover, as shown in FIG. 9B, by gripping the head section 83 and twisting in reverse, the upper side inclined guide sections 81b, 81b of the lateral axle section 81 of the extending section enter into the lower side of the slit 62b of the handle 61 and the slit 62b abuts against the step section 84 on the lower end of the head section 83, thereby engaging the handle 61 at a location where a small stroke is obtained.

By the operation described above, as shown in FIG. 8, the lower end 63 on the other end of the handle 61 becomes located at a relatively low position as indicated by the arrow D, and therefore when moved in the direction of the arrow A2 in FIG. 1, a relatively small stroke is possible and the negative pressure created during expression of milk is accordingly smaller.

Conversely, in FIG. 7A, the lower end 63 on the other end of the handle 61 is located at a relatively upper position as indicated by the arrow U, and therefore when moved in the direction of the arrow A2 in FIG. 1, a relatively large stroke is possible and the negative pressure created during expression of milk is accordingly larger.

In this way, in the present embodiment, it is possible to display a similar action and effect to those of the first embodiment.

Figure 12:
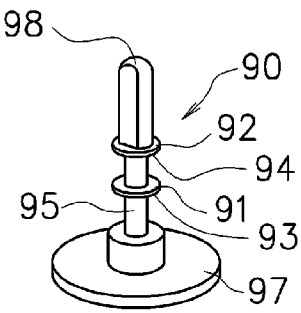
FIG. 12 is an enlarged perspective diagram showing the structure of an engaging section relating to a third embodiment of the present invention.

FIG. 12 is an enlarged perspective diagram showing the structure of a coupling member relating to a third embodiment of the invention.

This coupling member 90 is not attached rotatably with respect to the deforming section 32 as indicated by the arrow about a virtual central axis C of the extending section, as in the other embodiments. This embodiment is one example of a mode in which at least a plurality of engaging sections are provided on the extending section, along the direction of extension of the extending section.

Figure 15:
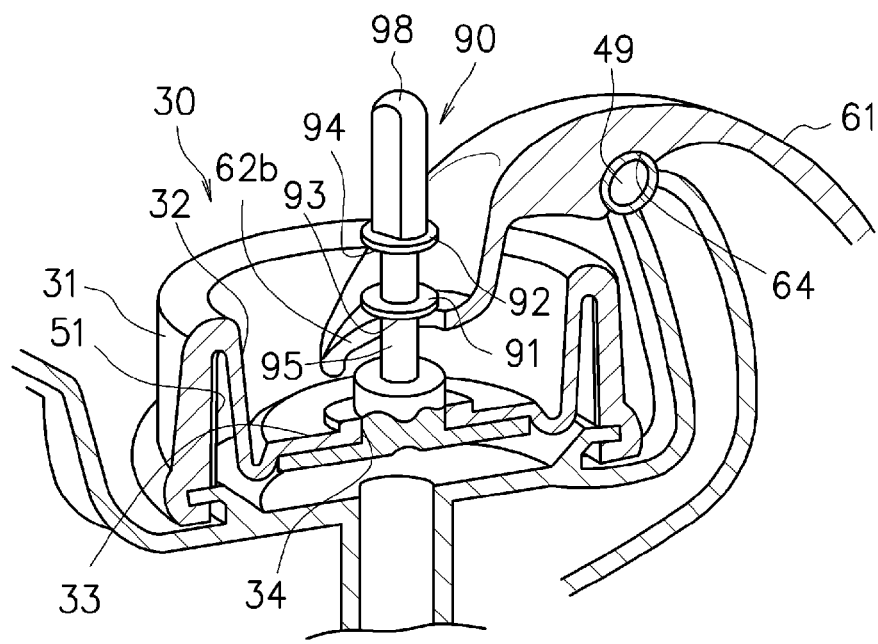
FIGS. 15A and 15B are partial enlarged cross-sectional diagrams showing a state where the engaging section in FIG. 12 and the engaged section on the operating section are intermeshed and engaged.
Figure 15:
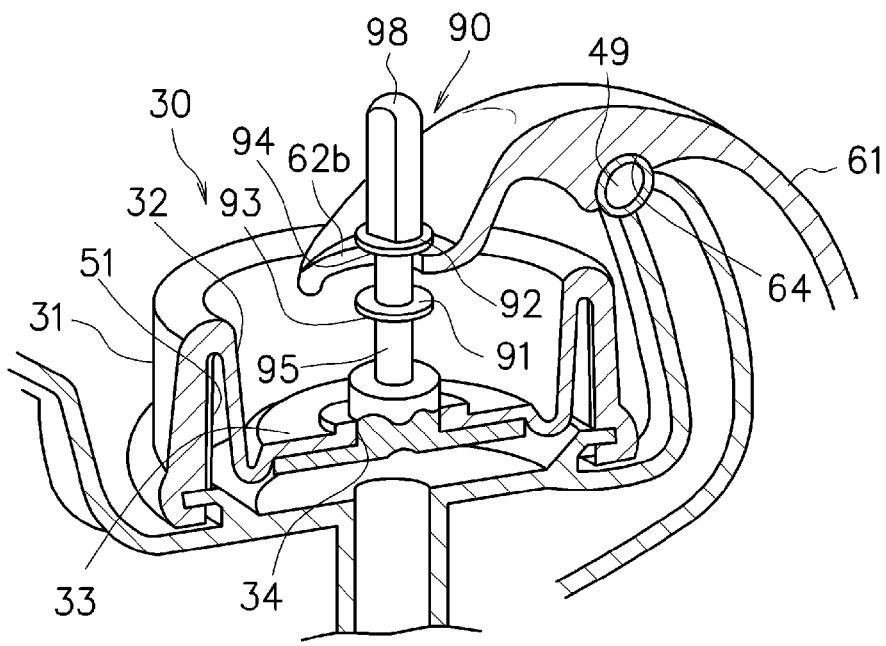

In FIG. 12, the lower portion of the axle-shaped extending section 95 of this coupling member 90 is inserted through a through hole 34 and fitted into the rear of the bottom surface section 33 of the deforming section, as shown in FIGS. 15A and 15B.

Therefore, when the coupling member 90 is tilted down, as described hereinafter, the coupling section 90 becomes inclined due to the elastic force of the deforming section 30.

Moreover, the coupling section 90 is formed with a plurality of engaging sections 91, 92 in a portion where the diameter is enlarged to a ring shape or flange shape, along an axle-shaped extending section that is erected perpendicularly in FIG. 12. The engaging section 92 is formed integrally with the lower end of the head section 98. There is a downward facing step section 93 on the engaging section 91, and there is a downward facing step section 94 on the engaging section 92 positioned thereabove.

Furthermore, the head section 98 provided on the front end section of the extending section 95 is a circular shape which is sufficiently large to be gripped by the user's hand and which extends to a long dimension in the vertical direction, and taking account in particular of the ease of gripping, the head section 98 is formed as a thin plate having a reduced thickness.

The coupling section 90 further has a low flat circular disk-shaped base section 97 of which the base end section is enlarged to a broad diameter. See FIG. 12.

The description will now be given with reference to FIGS. 13A and 13B and FIG. 14.

Figure 13:
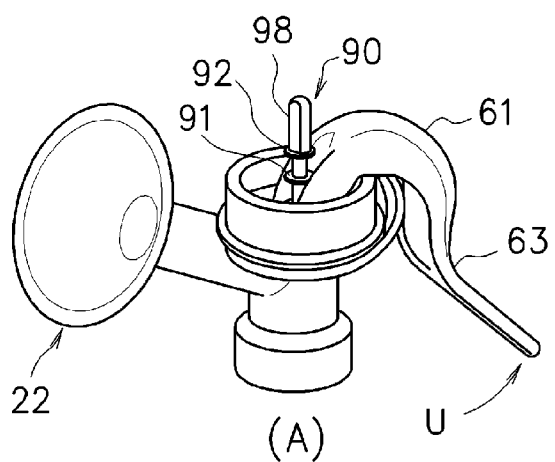
FIGS. 13A and 13B are partial schematic perspective diagrams showing an example of use of the engaging section in FIG. 12.
Figure 13:
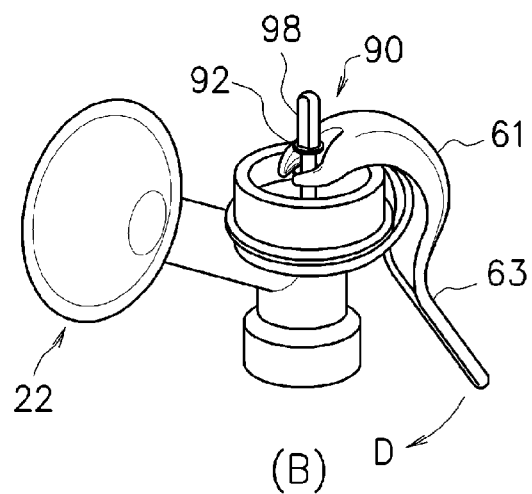

FIGS. 13A and 13B show states where the handle 61 has been engaged with the coupling member 90; in FIG. 13A, the upper end of the handle section 61 is inserted deeply into the very narrow bottomed cylinder of the deforming section 30, and the slit in the engaged section thereof is inserted to the extending section 95 as shown in FIG. 12. FIGS. 15A and 15B show enlarged partial cross-sectional diagrams of this state.

In FIG. 13B, the engaging section 91 of the coupling section 90 is engaged with the slit 62b, which is the engaged section of the handle section 61. FIG. 15B is a partial enlarged cross-sectional diagram of this state.

Here, as shown in FIG. 14, if the user grips the head section 98 of the coupling member 90 and tilts down the head section 98 in a direction away from the handle 61, then the bottom surface section 33 of the deforming section 30 in the vicinity of the lower end of the coupling member 90 deforms, and hence the coupling member 90 tilts down and consequently bends and becomes inclined as shown in FIG. 14. Consequently, the handle 61 can be disengaged easily from the engaging section 91 which is the engaging section with which the engaging section was engaged.

Thereupon, the engaged section of the handle 61 is moved slightly upwards. Next, when the user releases the head section 98 of the coupling member 90 from a gripped state, the coupling member 90 is restored due to the elastic properties thereof, and the slit 62b, which is the engaged section of the handle section 61 can be engaged with the engaging section 92 of the coupling section 90.

In this way, the engaging position of the engaged section of the handle 61 can be changed.

By the operation described above, as shown in FIG. 13B, the lower end 63 on the other end of the handle 61 becomes located at a relatively low position as indicated by the arrow D, and therefore when moved in the direction of the arrow A2 in FIG. 1, a relatively small stroke is possible and the negative pressure created during expression of milk is accordingly smaller.

Conversely, in FIG. 13A, the lower end 63 on the other end of the handle 61 is located at a relatively upper position as indicated by the arrow U, and therefore when moved in the direction of the arrow A2 in FIG. 1, a relatively large stroke is possible and the negative pressure created during expression of milk is accordingly larger.

In this way, in the present embodiment, it is possible to display a similar action and effect to those of the first embodiment.

The present invention is not limited to the embodiments described above.

For example, the coupling member which can be rotated about an axis is not limited to the shape and structure of the first and second embodiments, and it is possible to use any coupling member provided that it is possible to change the height position of an engaging section by rotating the coupling member about an axis.

A hook-shaped portion such as that provided in the head of the coupling section of the first embodiment may also be formed in the head sections of the coupling members according to the second and third embodiments.

Furthermore, the individual compositions of each embodiment are not necessarily required in their entirety, and a portion thereof can be omitted, in which case it is possible to adopt a combination of different compositions by combining other compositions which are not illustrated, or to use the respective compositions of the embodiments in a mutually combined fashion.

REFERENCE SIGNS LIST

11 accommodating vessel
20 breast pump
21 (breast pump) main body
22 milk expressing section
30 negative pressure generating member
31 (first) wall section
32 deforming section (second wall section)
33 bottom surface section
35 coupling section (member)
61 operating section (handle)
70, 80, 90 coupling section (member)

The invention claimed is:

1. A manual breast pump having an accommodating vessel for collecting breast milk, an attachment and detachment section for attaching and detaching a breast pump main body with respect to the accommodating vessel, and a manual operating section attached to the breast pump main body and deforming a negative pressure generating member installed on the breast pump main body, wherein
   the breast pump main body has an enlarged-diameter milk expressing section having an enlarged diameter for abutting against a user's breast;
   the negative pressure generating member comprises:
      a coupling section which has an extending section erected in the form of a pillar, and which is coupled with the operating section by an engaging section formed midway in the extending section; and
      a deforming section which generates the negative pressure by deforming, upon receiving a force from the coupling section,
   the manual operating section is a long handle and comprises:
      a bearing section supported on an axle section provided on the breast pump main body;
      an engaged section which is disposed at one end of the handle and coupled with the coupling section; and
      a lever section disposed at the other end of the handle, and wherein
      with the deforming section undergoing elastic deformation at the lower end of the coupling section, the extending section is configured to engage with the handle when erected and disengage from the handle when tilted down due to the elasticity of the deforming section,
      at least a plurality of the engaging sections are provided on the extending section along a direction of extension of the extending section, and
      a grippable head section is provided at a front end of the extending section.

2. The manual breast pump according to claim 1, wherein the grippable head section protrudes beyond the negative pressure generating member when the handle is in a non-operated state.

3. The manual breast pump according to claim 1, the grippable head section is formed as a thin plate having a reduced thickness.

* * * * *